United States Patent [19]

Heiliger

[11] Patent Number: 5,442,021

[45] Date of Patent: Aug. 15, 1995

[54] LUMINESCENT COPOLYMERS

[75] Inventor: Ludger Heiliger, Leverkusen, Germany

[73] Assignee: Bayer Aktiengesellschaft, Leverkusen, Germany

[21] Appl. No.: 198,637

[22] Filed: Feb. 18, 1994

[30] Foreign Application Priority Data

Feb. 26, 1993 [DE] Germany ............... 43 05 959.7

[51] Int. Cl.$^6$ ............... C08F 230/04; C08F 214/18; C08F 220/58; C08F 216/10; C08F 220/104

[52] U.S. Cl. ............... 526/241; 526/244; 526/304; 526/313; 526/318.1

[58] Field of Search ............... 526/241, 244, 304, 313, 526/318.1

[56] References Cited

U.S. PATENT DOCUMENTS

| 4,166,105 | 8/1979 | Hirschfeld ............... 424/8 |
| 5,298,583 | 3/1994 | Heiliger et al. ............... 526/286 |

FOREIGN PATENT DOCUMENTS

| 513560 | 11/1992 | European Pat. Off. . |
| 0959679 | 6/1964 | United Kingdom . |
| 959679 | 6/1964 | United Kingdom . |
| 8908682 | 9/1989 | WIPO . |

OTHER PUBLICATIONS

Lasermat: Matrix Assisted Laser Desorption Mass Spectrometry, Heiliger Petri In Alpha–Cyano, (Apr. 26, 1994.
Clin. Chem. 36:8 1497–1502 (1990).
Soini et al. "Applications in Biotechnology".
J. Inorg. Nucl. Chem., 28, 3005–3018 (1966).
J. Appl. Poly. Sci, 25, 2007–2017 (1980).
Anal. Chem., 62, 1841–1845 (1990).

*Primary Examiner*—Joseph L. Schofer
*Assistant Examiner*—Wu C. Cheng
*Attorney, Agent, or Firm*—Connolly and Hutz

[57] ABSTRACT

Luminescent copolymers having the following structure:

$$[A]_a\text{—}[B]_b$$

in which

A is a luminescent component,

B represents (co)monomers and a and b represent the percentages by weight of A and B in the copolymer, a making up 0.0001 to 20% by weight and b making up 99.9999 to 80% by weight, rare earth metal complexes having the formula $M^{3+}(L)_n$—suitable as component A in claim 1—where $M^{3+}$ is the cation of a rare earth metal, L is a polymerizable complex ligand and n is an integer of 1 to 4, as their initial product and the use of the luminescent copolymers in medical diagnosis.

4 Claims, No Drawings

LUMINESCENT COPOLYMERS

This invention relates to luminescent copolymers, to complex salts of rare earth metals (as their initial products), to processes for their production and to their use in medical diagnosis and for marking plastics. The copolymers are synthesized from special luminescent complex salts of rare earth metals as monomers and any comonomers. Luminescence is understood to be the emission of electromagnetic radiation (light) during the return of atoms from an excited state to their ground state. This transition may take place from an excited singlet state or an excited triplet state. The radiation emitted from a singlet state is known as fluorescence while the radiation emitted from a triplet state is known as phosphorescence. Phosphorescence requires a spin reversal between excitation and the release of energy which results in prolongation of the excited state, so that phosphorescence only begins after a certain delay.

Copolymers according to the invention are characterized in that
1. they contain luminescent complex salts of rare earth metals with a polymerizable double bond as monomers, the phosphorescence of the organic complex ligands being transmitted to rare earth metal ions which themselves then emit the energy taken up in the form of fluorescence, and
2. radical-polymerizable comonomers.

Polymers containing organic fluorescent groups are known. They are used in medical diagnostics as marking substances for biologically active molecules, such as for example proteins or nucleic acids (for example EP-A 513 560, U.S. Pat. No. 4,166,105). All organic fluorescent compounds compete with the background fluoresence, i.e. the natural fluorescence of the biological material (proteins, nucleic acids). The biological material has decay of its excited states in the same order of magnitude as the marking substances. This results in increased blank values which, in the measurement of the fluorescence of the marking substances, reduce the sensitivity of detection to well below the theoretically possible limit. The fluorescence of the metal cation is delayed by the relatively long life of the triplet state and by the transmission of its energy to the rare earth metal ion. It can still be measured when the emission of the biological materials (background fluorescence) has decayed. In principle, therefore, the relatively high signal-to-noise ratio provides for sensitive detection of the biological material and, hence, for relatively early recognition of potential pathogens.

Diagnostic detection methods using rare earth metals are known (CRC Crit. Rev. Anal. Chem. 1987, 18, 105–154; Scand. J. Clin. Lab. Invest. 1988, 48, 389–400). In this case, $Eu^{3+}$ metal cations are complexed with aminopolycarboxylic acids and bound to proteins (approx. 5 to 15 $Eu^{3+}$/protein), for example to streptavidin, or antibodies. After the proteins have carried out the immunological recognition reactions with their associated haptens or with the hapten-labeled gene probes—DNA hybrids, the actual detection is provided by luminescence. To this end, the non-luminescent $Eu^{3+}$ aminopolycarboxylic acid complex has to be destroyed and the $Eu^{3+}$ recomplexed with UV energy transfer ligands, which involves additional effort (washing processes, non-specific interactions). Because of the need for recomplexing, this method of detection is of only limited use. The luminescent copolymers according to the invention do not require recomplexing because they are stable under the in-use conditions. This simplifies the handling and conduct of the detection reactions.

More recent developments (Anal. Chem. 1990, 62, 1841–1845; Clin. Chem. 1990, 36, 1497–1502) describe $Eu^{3+}$ complexes which do not have to be recomplexed for the detection of proteins. In their case, however, each $Eu^{3+}$ ion is only complexed with one UV energy transfer molecule. However, to obtain high luminescence intensities which actually provide for sensitive detection in the first place, several UV absorber ligands are required for every metal ion, a maximum of four being possible (J. Inorg. Nucl. Chem. 1966, 28, 3005–3018). Accordingly, high sensitivity of detection can only be obtained in this method with multiple marking of the protein (up to 450 $Eu^{3+}$/protein) which is only possible in exceptional cases. The copolymers according to the invention have high luminescence intensity because they contain up to four UV energy transfer ligands per metal ion. In addition, the copolymers according to the invention reach a far larger $Eu^{3+}$/protein ratio (typically between $10^3$ and $10^5$) than those hitherto described. Since the copolymers according to the invention are not metal-ion-labeled proteins (or other biomaterials), but rather synthetic polymers containing metal ions, they may even be used under conditions where proteins would normally be denatured (high temperature, high ionic strength of the solution). Polymers containing rare earth metals are known and are described, for example, in J. Appl. Pol. Sci. 1980, 25, 2007–2017, according to which UV energy transfer ligands are incorporated in polymers as complex ligands for $Eu^{3+}$ and charged with $Eu^{3+}$. It was found that the multiple coordination of a metal ion with the polymeric ligands is seriously restricted by the increasing steric hindrance and decreasing free mobility of the single bonds. Above all, the highly luminescent tetra-coordinated complex is not formed at all.

The copolymers according to the invention contain rare earth metal cations tetra-coordinated with UV energy transfer ligands. The cations are complexed before polymerization and the complex thus formed is polymerized. Accordingly, the copolymers according to the invention are far superior in luminescence intensity to the copolymers described in the literature.

The copolymers according to the invention are also suitable for marking plastics to make them distinguishable.

The copolymers according to the invention contain the following components:

$$[A]_a\text{—}[B]_b$$

in which
A is a luminescent component,
B represents (co)monomers and
a and b represent the percentages by weight of A and B, a making up 0.0001 to 20% by weight and b making up 99.9999 to 80% by weight.

The luminescent component A is a complex salt of a rare earth metal corresponding to the following formula:

$$M^{3+}(L)_n$$

in which

M stands for rare earth metal cations, such as Dy, Sm, Eu, Tb and

L stands for bidentate ligands containing a conjugated π-system and at least one oxygen or nitrogen atom and at least one polymerizable C=C bond.

This also includes cyclic and in particular aromatic compounds. The ligands have to be adapted to the central metal ion in such a way that energy can be transferred, i.e. the emission wavelength of the phosphorescence of the ligands must only be at most 50 nm smaller than the absorption wavelength of the metal ion.

n is an integer of 1 to 4, preferably 3 or 4 and, more preferably, 4.

The following ligands are preferred:

1.

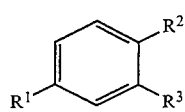

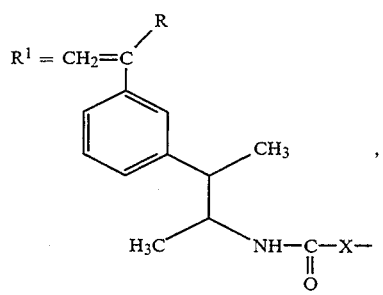

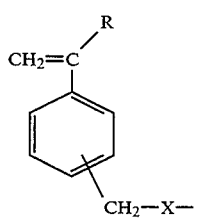

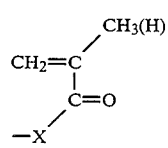

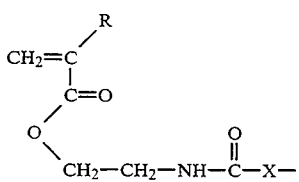

X = NH, O, S; R* = H, CH$_3$

R$^2$ = R$^3$ COOM, PO$_3$M, PO$_2$M, OH, NH$_2$, SM, H

M = Na, K, NH$_4$, H

2.

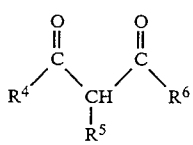

R$^4$ = (CH$_2$=CH—)$_n$—,

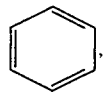,

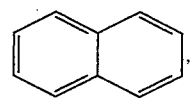,

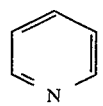

and

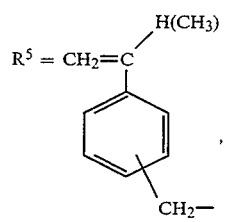,

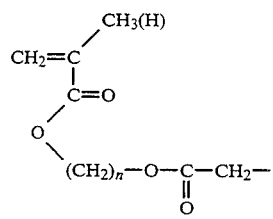

R$^6$ = C$_n$F$_{2n+1}$, C$_n$H$_{2n+1}$ n = 1-8

3.

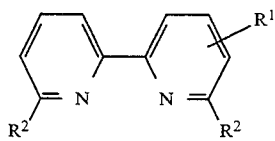

R$^1$, R$^2$, R$^3$ as described above

The following are particularly preferred luminescent components:

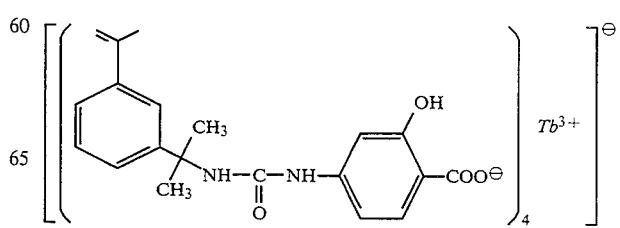

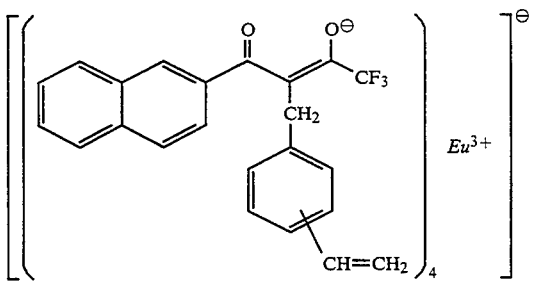

The polymerizable ligands are formed by the reaction suitable monomers bearing functional groups, such as for example (meth)acrylic acid chloride, isocyanatoethyl methacrylate, isopropenyl-α,α-dimethylbenzyl isocyanate, chloromethyl styrene, chloroacetoxypropyl or ethyl methacrylate, with suitable UV energy transfer ligands via alkyl, ester, acid amide, urethane, urea and/or thiourea groups.

The following are suitable (co)monomers B: α,β-unsaturated compounds, such as styrene, α-methyl styrene, vinyltoluene, substituted vinyltoluenes, vinyl puridine, acrylonitrile and esters of acrylic and methacrylic acid. Esters of (meth)acrylic acid containing 1 to 20 carbon atoms in the alcohol component are preferred, including for example methyl (meth)acrylate, ethyl (meth)acrylate, n-propyl (meth)acrylate, isopropyl (meth)acrylate, n-butyl (meth)acrylate, isobutyl (meth)acrylate, tert.butyl (meth)acrylate and 2-ethylhexyl (meth)acrylate. Methacrylic acid esters of cycloaliphatic alcohols, such as cyclohexyl methacrylate, furfuryl methacrylate; vinyl esters, such as vinyl acetate, vinyl propionate; maleic anhydride, itaconic anhydride, are also suitable; the monomers B may also be mixed with one another in various ratios.

The percentage by weight of a in the copolymers according to the invention is from 0.0001 to 20% by weight, preferably from 0.01 to 10% by weight and, more preferably, from 0.1 to 5% by weight.

The percentage content of b is from 99.9999 to 80% by weight, preferably from 99.99 to 90% by weight and, more preferably, from 99.9 to 95% by weight.

The copolymers according to the invention may be uncrosslinked (linear) with molecular weights in the range from 1,000 to 10,000,000 and preferably in the range from 5,000 to 1,000,000. Preferably, however, they are not crosslinked. The copolymers according to the invention may be present in the form of an aqueous dispersion with polymer particles from 30 to 5,000 nm, preferably from 40 to 2,000 nm and, more preferably, from 50 to 2,000 nm in diameter.

Particularly preferred comonomers B of the copolymers according to the invention for diagnostic applications are polar monomers, such as (methyl)methacrylate, ethylene glycol dimethacrylate, optionally together with water-soluble monomers, such as acrylonitrile, (meth)acrylic acid, hydroxyethyl (meth)acrylate, dimethyl aminoethyl methacrylate, which are capable of suppressing the non-specific interactions with biomaterials. The copolymers according to the invention are preferably used in the form of aqueous dispersions with polymer particles from 30 to 6,000 nm, preferably from 40 to 3,000 nm and more preferably from 40 to 2,000 nm in diameter. Ratios of metal$^{3+}$ to protein of $10^2$ to $10^7$ can be achieved, depending on the particle diameter.

The aqueous dispersions may be prepared by known methods of emulsion or suspension polymerization, for example using azo-bis-isobutyronitrile, benzoyl peroxide or alkali or ammonium peroxydisulfate as radical initiators. To this end, the generally water-insoluble luminescent components A and the comonomers B are emulsified or dispersed in water with an emulsifier or dispersant and then polymerized. Suitable emulsifiers and dispersants are, for example, alkali metal or ammonium salts of alkyl sulfates and alkyl sulfonates ($C_{8-22}$), alkyl benzenesulfonates ($C_{6-15}$) or fatty acids. Polymeric emulsifiers or dispersants, such as for example polyvinyl pyrrolidone, polyvinyl alcohol or saponified and partly saponified styrene/maleic anhydride copolymers or the polyester urethanes described in EP-A 334 032, may also be used. Polystyrene or polymethyl methacrylate latices or dispersions, for example, are suitable for use as the seed latex. The latex or dispersion may be freed from any molecularly dissolved constituents remaining by centrifugation. This product may be directly covalently bonded to biologically relevant molecules, such as for example proteins, antibodies, aminated gene probes, via a carbodiimide coupling and used in diagnostic detection systems.

Where the copolymers according to the invention are used for marking plastics, the choice of the monomers B is governed by the plastic. For example, methyl methacrylate or acrylamide is particularly preferred as the monomer B for marking polymethyl methacrylate or polyamides, such as polyamide-6 or polyamide-6,6. Styrene is particularly preferred as the monomer B for marking polystyrene, styrene/butadiene copolymer and poly-(hydroxy-carbonyloxy-1,4-phenyleneisopropylidene-1,4-phenylene). Stearyl methacrylate, optionally together with methyl methacrylate in a ratio by weight of 10:1 to 30:1, is particularly preferred as the monomer B for marking polyethylene, polypropylene and copolymers thereof, such as ethylene/vinyl acetate copolymer. A mixture of 72% by weight styrene and 28% by weight acrylonitrile is particularly preferred as the comonomer B for marking polyethylene terephthalate, styrene/butadiene/acrylonitrile terpolymer and styrene/acrylonitrile copolymer.

Already marked plastics may be used as markers for other plastics. Thus, a polymethyl methacrylate marked with a copolymer according to the invention of a luminescent component A and methyl methacrylate as the monomer B may be used for marking polyamides.

The copolymers according to the invention for marking plastics may be produced by emulsion polymerization, the copolymer isolated from the latex rather than the latex itself being used for marking. Plastics may be marked with the copolymers according to the invention (or blends thereof) by mechanical mixing, kneading and/or extrusion. For example, the plastic to be marked may be mixed, kneaded or extruded with the copolymer according to the invention at a temperature at least 10° C. above the softening temperature of the component with the highest softening temperature. The copolymer according to the invention is normally used in a quantity of 0.001 to 10% by weight, preferably in a quantity of 0.005 to 5% by weight and more preferably in a quantity of 0.01 to 2% by weight, based on the marked plastic.

EXAMPLES

Luminescent Components

Example 1 a) 0.05 mol (7.65 g) p-aminosalicylic acid are refluxed for 6 hours with 0.05 mol (10.05 g) m-TMI® (α,α-dimethyl-m-isopropylbenzylisocyanate) and a spatula tip of 2,6-bis-t.butylphenol in 100 ml anhydrous acetone. The precipitate formed is removed by filtration under suction, washed with cold acetone and dried. $^1$H-NMR and IR analysis show N-(α,α-dimethyl-m-isopropenylbenzyl)-N'-(p-salicyl)-urea as a pure product ($\delta^1$H 6.7 and 8.8 ppm, $\nu_{C-H}$ urea=1,630 cm$^{-1}$). Yield approx. 63 %.

b) NH$_4$ [Tb(C$_{20}$H$_{21}$N$_2$O$_4$)$_4$]0.2 g of the ligand from Example 1a) and 0.06 g Tb(NO$_3$)$_3$.5H$_2$O are separately dissolved in 3 ml methanol. The two solutions are combined and 0.5 ml concentrated ammonia solution is added dropwise, resulting in the formation of a precipitate. It is removed by filtration under suction, washed with water and dried in a high vacuum. The $^{159}$Tb content (10.1% Tb) was determined by elemental analysis.

Example 2 a) 0.05 mol (13.25 g) 1-(2-naphthoyl)-3,3,3-trifluoroacetone are dissolved in 50 ml methanol. 0.05 mol (11.32 g) sodium methanolate is then slowly added at 0° C. from a 30% by weight sodium methanolate solution in methanol, followed by heating to room temperature. After the addition of 0.05 mol (7.63 g) chloromethyl styrene, the reaction mixture is refluxed for 16 hours. The fine precipitate (NaCl) formed is filtered off and the solution is concentrated in aspirator vacuum to approx. ⅓rd of its original volume, followed by the addition of water in such a quantity that the precipitate formed just dissolves. The organic phase is separated off, the aqueous phase is extracted twice by shaking with chloroform and the combined organic phases are dried over sodium sulfate, filtered and concentrated by evaporation. The crude products are purified in a solvent mixture of toluene: methylene chloride; ethyl acetate: methanol (ratio 5:3:1:0.5) in a column of silica gel (0.063 to 0.2 mm). ($\delta^{19}$F-76.6 ppm). Yield of 1-(2-naphthoyl)-l-chloromethyl styrene-3,3,3-trifluoroacetone: approx. 25% of the theoretical.

b) NH$_4$[Eu(C$_{23}$H$_{16}$F$_3$O$_2$)$_4$]0.1 g ligand from Example 2a) and 0.023 g EuCl$_3$.6H$_2$O are separately dissolved in 2 ml methanol. the two solutions are combined and 0.2 ml concentrated ammonia solution is added dropwise, resulting in the formation of a precipitate. The precipitate is filtered off under suction, washed with water and dried in a high vacuum. The $^{152}$Eu content (9.0% Eu) was determined by elemental analysis.

Copolymers as Markers for Polyethylene (PE)

Example 3

0.25 g EuCl$_3$.6H$_2$O, 1.575 g of the substance of Example 2a) and 0.645 g N,N-dimethylaminoethyl methacrylate are dissolved in 135.5 ml methanol and complexing is verified by UV excitation at 366 nm (strong red luminescence). 3.57 g ethylene glycol dimethacrylate, 28.5 g stearyl methacrylate and 0.35 g azo-bis-isobutyronitrile are then added, after which the apparatus is evacuated and purged with high-purity nitrogen (this operation is repeated another two times) and heated to 65° C. A white precipitate appears after only a few hours, the entire mixture having completely precipitated after a reaction time of 16 h. The precipitate is filtered off under suction, washed with methanol and dried. Yield: 90% of the theoretical of a powder emitting bright red luminescence under UV excitation.

Example 4

As in Example 3, 0.25 g Tb(NO$_3$)$_3$.5H$_2$O are complexed with 1.23 g of the substance of Example 1a) and 0.55 g N,N'-dimethylaminoethyl methacrylate in 54.9 ml dimethyl acetamide (green luminescence after excitation at 366 nm) and the complex formed is polymerized for 16 h at 65° C. after addition of 1.72 g ethylene glycol dimethacrylate, 13.7 g stearyl methacrylate and 0.17 g azo-bis-isobutyronitrile. After removal of the precipitate by filtration under suction and washing with methanol, the filtrate is precipitated in methanol, filtered under suction, washed and dried. Yield: 89% of theoretical of a powder emitting bright green luminescence under UV excitation.

Copolymers as Markers for Polymethyl Methacrylate

Examples 5 and 6

Examples 3 and 4 are repeated with the following changes: stearyl methacrylate is replaced by the same quantity of methyl methacrylate.

Incorporation of the Polymer Markers in Polyethylene

Example 7

A Haake rheometer kneader (holding capacity 50 ml) is heated to 130° C. and filled with 44 g polyethylene granules (LDPE; Novex Exp. 2184). After kneading for 10 minutes, 0.37 g of the substance of Example 3 and 0,185 g of the substance of Example 4 are added, followed by kneading for another 15 minutes at the same temperature. Accordingly, the polymer contains approx. 20 to 25 ppm metal ions and the same quantity of dyes.

Incorporation of the Polymer Markers in Polymethyl Methacrylate

Example 8

Example 7 is repeated with the following changes: the polyethylene granules are replaced by granulated polymethyl methacrylate (Röhm GmbH, Darmstadt) while the substances of Examples 3 and 4 are replaced by the products of Examples 5 and 6 and the kneader temperature is kept at 200° C.

Production of Copolymers for Diagnostic Applications

Example 9

0.25 g EuCl$_3$.6H$_2$O, 1.575 g of the substance of Example 2 and 0.645 g N,N'-dimethylaminoethyl methacrylate are dissolved in 135.5 ml methanol and complexing is verified by UV excitation at 366 nm (bright red luminescence). The methanol is then distilled off in a high vacuum at room temperature and 3.57 g ethylene glycol dimethacrylate and 28.5 g methyl methacrylate are added. The resulting solution is added to an aqueous dispersion of 8 g polyester urethane according to EP-A 334 032 (Example oligourethane 1, 0.6 g 4,4'-azo-bis-(4-cyanopentane carboxylic acid) and 700 ml deionized water, followed by stirring for 30 minutes, heating to 65° C. and stirring for another 16 hours. The crude emulsion is filtered through a 30 μm mesh polyamide cloth and freed from any monomeric impurities by 3x centrifgation and refilling with deionized water. The pH value of the emulsion is adjusted to 8.5 with sodium hydroxide. The emulsion contains particles with a diameter of 140 nm corresponding to approx. 12,000 $Eu^{3+}$ metal atoms per latex particle.

The detection limit of the emulsion under normal flashlight excitation at 331 nm and detection 615 nm is $10^{11}$ mol $Eu^{3+}$ ions per liter, i.e. at approx. $10^{-15}$ mol latex particles per liter. The quantum yield of the latex solution under irradiation of 331 nm is 15%. The emulsion may be directly used for marking proteins, such as for example streptavidin, biologically relevant antibodies or or aminated gene probes.

Example 10

Example 9 is repeated with the following change:

The 0.25 g $EuCl_3.6H_2O$ and 1.575 g substance of Example 2 are replaced by 0.38 g $Tb(NO_3)_3.5H_2O$ and 1,45 g of the substance of Example 1. The resulting latex has an average particle diameter of 120 nm and fluoresces at 546 nm under excitation at 333 nm. The $Tb^{3+}$ concentration works out at 7,500 per latex particle.

I claim:

1. Luminescent copolymers having the formula:

$[A]_a$—$[B]_b$ in which

A is a rare earth metal complex having the formula $M^{3+}(L)_n$, wherein $M^{3+}$ is a rare earth metal cation, L is a polymerizable complex ligand containing a polymerizable double bond, and n is an integer of 1 to 4; and B represents radical-polymerizable (co)monomers; and a and b represent the percentages by weight of A and B in the copolymer a; a making up 0.0001 to 20% by weight and b making up 99.9999 to 80% by weight of the luminescent copolymer.

2. A luminescent copolymer as claimed in claim 1, wherein $M^{3+}$ is an ion of europium or terbium.

3. A luminescent copolymer as claimed in claim 1 wherein A is a rare earth metal complex having one of the following formulae:

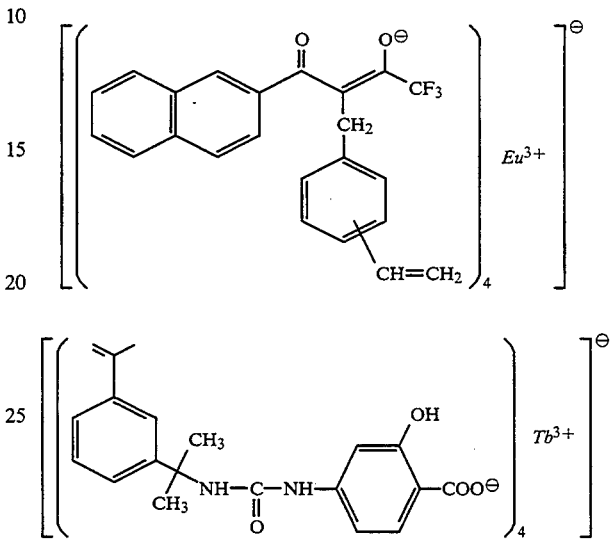

4. A luminescent copolymer as claimed in claim 1, wherein the polymerizable complex ligand is a bidentate ligand containing a conjugated π-system and at least one oxygen or nitrogen atom and at least one polymerizable C=C bond.

* * * * *